United States Patent
LaFontaine et al.

(10) Patent No.: US 6,443,158 B1
(45) Date of Patent: Sep. 3, 2002

(54) PERCUTANEOUS CORONARY ARTERY BYPASS THROUGH A VENOUS VESSEL

(75) Inventors: Daniel M. LaFontaine, Plymouth; Kent D. Harrison, Maple Grove; Chad J. Kugler, Andover; John M. K. Daniel, Plymouth, all of MN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/088,496

(22) Filed: Jun. 1, 1998

Related U.S. Application Data

(60) Provisional application No. 60/050,257, filed on Jun. 19, 1997.

(51) Int. Cl.⁷ .............................................. A61B 19/00
(52) U.S. Cl. ......................................... 128/898; 604/8
(58) Field of Search ............................... 128/898; 604/8

(56) References Cited

U.S. PATENT DOCUMENTS

| | | |
|---|---|---|
| 3,667,069 A | 6/1972 | Blackshear et al. ................ 3/1 |
| 4,016,884 A | 4/1977 | Kwan-Gett ................ 128/348 |
| 4,165,747 A | 8/1979 | Bermant ..................... 128/334 |
| 4,173,981 A | 11/1979 | Mortensen ................. 128/348 |
| 4,190,909 A | 3/1980 | Ablaza ........................... 3/1.4 |
| 4,230,096 A | 10/1980 | Zeff et al. ................... 128/1 R |
| 4,546,499 A | 10/1985 | Possis et al. ................... 623/1 |

(List continued on next page.)

FOREIGN PATENT DOCUMENTS

| | | |
|---|---|---|
| EP | 0 769 272 A1 | 4/1997 |
| JP | 97-281410 | 7/1997 |
| SU | 388738 | 9/1971 |
| SU | 891076 | 12/1981 |
| SU | 1822750 A1 | 7/1982 |
| SU | 308752 | 7/1991 |
| SU | 1600708 | 12/1995 |

(List continued on next page.)

OTHER PUBLICATIONS

"The Current Status of Lasers in the Treatment of Cardiovascular Disease" by Jeffrey M. Isner and Richard H. Clarke, *IEEE*, vol. QE–20, No. 12, Dec. 1984, pp. 1406–1420.

"The Possibility of Myocardial Revascularization by Creation of a Left Ventriculocoronary Artery Fistula", by Ian Munro and Peter Allen, M.D. , *Journal of Thoracic and Cardiovascular Surgery*, vol. 58, No. 1, Jul. 1969, pp. 25–32.

*Primary Examiner*—Corrine McDermott
*Assistant Examiner*—Thomas C. Barrett
(74) *Attorney, Agent, or Firm*—Westman, Champlin & Kelly, P.A.

(57) ABSTRACT

A bypass system for bypassing a restriction in a parent vessel of a mammal to provide blood flow past the restriction. The bypass system couples a restricted artery to a venous vessel distal of a restriction to provide blood flow through the artery distal of the restriction. Blood flow is provided to a distal portion of the artery through an adjacent venous vessel so that blood can be provided to distal portions of the restricted artery.

12 Claims, 14 Drawing Sheets

U.S. PATENT DOCUMENTS

| | | | |
|---|---|---|---|
| 4,562,597 A | 1/1986 | Possis et al. | 623/1 |
| 4,566,453 A | 1/1986 | Kumano et al. | 128/303.1 |
| 4,601,718 A | 7/1986 | Possis et al. | 623/1 |
| 4,610,661 A | 9/1986 | Possis et al. | 604/52 |
| 4,667,673 A | 5/1987 | Li | 128/334 C |
| 4,690,684 A | 9/1987 | McGreevy et al. | 623/12 |
| 4,710,192 A | 12/1987 | Liotta et al. | 623/1 |
| 4,721,109 A | 1/1988 | Healey | 128/334 R |
| 4,790,819 A | 12/1988 | Li et al. | 604/59 |
| 4,803,984 A | 2/1989 | Narayanan et al. | 128/334 R |
| 4,808,163 A | 2/1989 | Laub | 604/105 |
| 4,819,640 A | 4/1989 | Narayanan et al. | 128/334 R |
| 4,827,931 A | 5/1989 | Longmore | 128/334 R |
| 4,907,591 A | 3/1990 | Vasconcellos et al. | 606/154 |
| 4,911,164 A | 3/1990 | Roth | 606/148 |
| 4,995,857 A | 2/1991 | Arnold | 600/16 |
| 5,011,469 A | 4/1991 | Buckberg et al. | 604/4 |
| 5,037,428 A | 8/1991 | Picha et al. | 606/155 |
| 5,047,039 A | 9/1991 | Avant et al. | 606/148 |
| 5,053,041 A | 10/1991 | Ansari et al. | 606/148 |
| 5,053,043 A | 10/1991 | Gottesman et al. | 606/148 |
| 5,061,245 A | 10/1991 | Waldvogel | 604/170 |
| 5,067,958 A | 11/1991 | Sandhaus | 606/142 |
| 5,080,663 A | 1/1992 | Mills et al. | 606/144 |
| 5,080,664 A | 1/1992 | Jain | 606/148 |
| 5,104,402 A | 4/1992 | Melbin | 623/1 |
| 5,144,961 A | 9/1992 | Chen et al. | 128/898 |
| 5,222,962 A | 6/1993 | Burkhart | 606/148 |
| 5,222,963 A | 6/1993 | Brinkerhoff et al. | 606/153 |
| 5,222,971 A | 6/1993 | Willard et al. | 606/158 |
| 5,234,445 A | 8/1993 | Walker et al. | 606/148 |
| 5,254,113 A | 10/1993 | Wilk | 606/8 |
| 5,281,236 A | 1/1994 | Bagnato et al. | 606/139 |
| 5,282,810 A | 2/1994 | Allen et al. | 606/150 |
| 5,287,861 A | 2/1994 | Wilk | 128/898 |
| 5,308,320 A | 5/1994 | Safar et al. | 604/4 |
| 5,314,436 A | 5/1994 | Wilk | 606/153 |
| 5,314,472 A | 5/1994 | Fontaine | 623/12 |
| 5,323,789 A | 6/1994 | Berggren et al. | 128/898 |
| 5,330,486 A | 7/1994 | Wilk | 606/139 |
| 5,370,683 A | 12/1994 | Fontaine | 623/1 |
| 5,382,257 A | 1/1995 | Lewis et al. | 606/148 |
| 5,383,854 A | 1/1995 | Safar et al. | 604/98 |
| 5,383,928 A | 1/1995 | Scott et al. | 623/1 |
| 5,397,345 A | 3/1995 | Lazarus | 623/1 |
| 5,403,333 A | 4/1995 | Kaster et al. | 606/151 |
| 5,409,019 A | 4/1995 | Wilk | 128/898 |
| 5,425,705 A | 6/1995 | Evard et al. | 604/28 |
| 5,425,739 A | 6/1995 | Jessen | 606/155 |
| 5,429,144 A | 7/1995 | Wilk | 128/898 |
| 5,433,700 A | 7/1995 | Peters | 604/4 |
| 5,437,684 A | 8/1995 | Calabrese et al. | 606/153 |
| 5,441,507 A | 8/1995 | Wilk | 606/139 |
| 5,443,497 A | 8/1995 | Venbrux | 623/1 |
| 5,447,512 A | 9/1995 | Wilson et al. | 606/139 |
| 5,449,372 A | 9/1995 | Schmaltz et al. | 606/198 |
| 5,452,733 A | 9/1995 | Sterman et al. | 128/898 |
| 5,456,714 A | 10/1995 | Owen | 623/1 |
| 5,472,404 A | 12/1995 | Volgushev | 600/36 |
| 5,501,698 A | 3/1996 | Roth et al. | 606/205 |
| 5,522,884 A | 6/1996 | Wright | 623/2 |
| 5,527,319 A | 6/1996 | Green et al. | 606/143 |
| 5,527,324 A | 6/1996 | Krantz et al. | 606/155 |
| 5,536,251 A | 7/1996 | Evard et al. | 604/93 |
| 5,540,677 A | 7/1996 | Sinofsky | 606/8 |
| 5,540,701 A | 7/1996 | Sharkey et al. | 606/153 |
| 5,545,171 A | 8/1996 | Sharkey et al. | 606/148 |
| 5,554,162 A | 9/1996 | DeLange | 606/153 |
| 5,556,414 A | 9/1996 | Turi | 606/198 |
| 5,556,428 A | 9/1996 | Shah | 623/13 |
| RE35,352 E | 10/1996 | Peters | 604/4 |
| 5,562,728 A | 10/1996 | Lazarus et al. | 623/1 |
| 5,569,272 A | 10/1996 | Reed et al. | 606/151 |
| 5,569,274 A | 10/1996 | Rapacki et al. | 606/158 |
| 5,571,090 A | 11/1996 | Sherts | 606/144 |
| 5,571,215 A | 11/1996 | Sterman et al. | 623/66 |
| 5,584,803 A | 12/1996 | Stevens et al. | 604/4 |
| 5,588,949 A | 12/1996 | Taylor et al. | 600/166 |
| 5,591,179 A | 1/1997 | Edelstein | 606/144 |
| 5,591,212 A | 1/1997 | Keimel | 607/5 |
| 5,593,424 A | 1/1997 | Northrup, III | 606/232 |
| RE35,459 E | 2/1997 | Junkman | 604/164 |
| 5,601,576 A | 2/1997 | Garrison | 606/148 |
| 5,601,581 A | 2/1997 | Fogarty et al. | 606/159 |
| 5,609,598 A | 3/1997 | Laufer et al. | 606/142 |
| 5,613,937 A | 3/1997 | Garrison et al. | 600/201 |
| 5,618,270 A | 4/1997 | Orejola | 604/164 |
| 5,643,292 A | 7/1997 | Hart | 606/144 |
| 5,653,744 A | 8/1997 | Khouri | 623/1 |
| 5,655,548 A | 8/1997 | Nelson et al. | 128/898 |
| 5,662,124 A | 9/1997 | Wilk | 128/898 |
| 5,662,711 A | 9/1997 | Douglas | 623/12 |
| 5,676,670 A | 10/1997 | Kim | 606/108 |
| 5,682,906 A | 11/1997 | Sterrman et al. | 128/898 |
| 5,685,857 A | 11/1997 | Negus et al. | 604/170 |
| 5,693,083 A | 12/1997 | Baker et al. | 623/1 |
| 5,702,368 A | 12/1997 | Stevens et al. | 604/171 |
| 5,702,412 A | 12/1997 | Popov et al. | 606/159 |
| 5,715,832 A | 2/1998 | Koblish et al. | 128/754 |
| 5,716,367 A | 2/1998 | Koike et al. | 606/144 |
| 5,718,725 A | 2/1998 | Sterman et al. | 623/2 |
| 5,722,426 A | 3/1998 | Kolff | 128/898 |
| 5,725,537 A | 3/1998 | Green et al. | 606/143 |
| 5,727,569 A | 3/1998 | Benetti et al. | 128/898 |
| 5,728,151 A | 3/1998 | Garrison et al. | 623/2 |
| 5,735,290 A | 4/1998 | Sterman et al. | 128/898 |
| 5,738,649 A | 4/1998 | Macoviak | 604/43 |
| 5,738,652 A | 4/1998 | Boyd et al. | 604/96 |
| 5,749,892 A | 5/1998 | Vierra et al. | 600/204 |
| 5,752,526 A | 5/1998 | Cosgrove | 128/898 |
| 5,755,682 A | 5/1998 | Knudson et al. | 604/8 |
| 5,755,687 A | 5/1998 | Donlon | 604/53 |
| 5,755,778 A | 5/1998 | Kleshinski | 623/1 |
| 5,758,663 A | 6/1998 | Wilk et al. | 128/898 |
| 5,766,151 A | 6/1998 | Valley et al. | 604/96 |
| 5,769,812 A | 6/1998 | Stevens et al. | 604/4 |
| 5,792,094 A | 8/1998 | Stevens et al. | 604/4 |
| 5,795,325 A | 8/1998 | Valley et al. | 604/53 |
| 5,797,920 A | 8/1998 | Kim | 606/108 |
| 5,797,933 A | 8/1998 | Snow et al. | 606/151 |
| 5,799,661 A | 9/1998 | Boyd et al. | 128/898 |
| 5,800,450 A | 9/1998 | Lary et al. | 606/180 |
| 5,800,522 A | 9/1998 | Campbell et al. | 623/1 |
| 5,830,222 A * | 11/1998 | Makower | 606/159 |
| 5,836,311 A | 11/1998 | Borst et al. | 128/897 |
| 5,855,210 A | 1/1999 | Sterman et al. | 128/898 |
| 5,855,614 A | 1/1999 | Stevens et al. | 623/11 |
| 5,868,770 A | 2/1999 | Rygaard | 606/167 |
| 5,921,979 A | 7/1999 | Kovac et al. | 606/1 |
| 5,928,181 A | 7/1999 | Coleman et al. | 604/8 |
| 6,190,353 B1 * | 2/2001 | Makower | 604/95 |

FOREIGN PATENT DOCUMENTS

| | | |
|---|---|---|
| WO | WO 95/08364 | 3/1995 |
| WO | WO 95/10218 | 4/1995 |
| WO | WO 95/15192 | 6/1995 |
| WO | WO 95/16476 | 6/1995 |
| WO | WO 96/10375 | 4/1996 |
| WO | WO 96/17644 | 6/1996 |
| WO | WO 96/25886 | 8/1996 |
| WO | WO 96/30072 | 10/1996 |

| | | | | | | |
|---|---|---|---|---|---|---|
| WO | WO 96/30073 | 10/1996 | | WO | WO 98/31302 | 7/1998 |
| WO | WO 96/32882 | 10/1996 | | WO | WO 98/32380 | 7/1998 |
| WO | WO 97/12555 | 4/1997 | | WO | WO 98/35626 | 8/1998 |
| WO | WO 97/13463 | 4/1997 | | WO | WO 98/37814 | 9/1998 |
| WO | WO 97/13468 | 4/1997 | | WO | WO 98/51223 | 11/1998 |
| WO | WO 97/13471 | 4/1997 | | WO | WO 98/52475 | 11/1998 |
| WO | WO 97/26939 | 7/1997 | | WO | WO 98/57590 | 12/1998 |
| WO | WO 97/37984 | 10/1997 | | WO | WO 98/57591 | 12/1998 |
| WO | WO 97/40751 | 11/1997 | | WO | WO 98/57592 | 12/1998 |
| WO | WO 98/06356 | 2/1998 | | WO | WO 99/04836 | 2/1999 |
| WO | WO 98/07399 | 2/1998 | | WO | WO 99/04845 | 2/1999 |
| WO | WO 98/10714 | 3/1998 | | WO | WO 99/35975 | 7/1999 |
| WO | WO 98/15237 | 4/1998 | | WO | WO 99/35977 | 7/1999 |
| WO | WO 98/16161 | 4/1998 | | WO | WO 99/35978 | 7/1999 |
| WO | WO 98/16174 | 4/1998 | | WO | WO 99/35979 | 7/1999 |
| WO | WO 98/17182 | 4/1998 | | WO | WO 99/35980 | 7/1999 |
| WO | WO 98/17187 | 4/1998 | | WO | WO 99/36000 | 7/1999 |
| WO | WO 98/19607 | 5/1998 | | WO | WO 99/36001 | 7/1999 |
| WO | WO 98/19634 | 5/1998 | | | | |
| WO | WO 98/19636 | 5/1998 | | | | |

* cited by examiner

PERCUTANEOUS CORONARY ARTERY BYPASS THROUGH A VENOUS VESSEL

The present application claims priority of U.S. Provisional patent application Ser. No. 60/050,257, filed Jun. 19, 1997.

The following U.S. patent applications are hereby fully incorporated:

U.S. Pat. No. 6,213,126, entitled PERCUTANEOUS ARTERY TO ARTERY BYPASS USING HEART TISSUE AS A PORTION OF A BYPASS CONDUIT, filed on even date herewith and assigned to the same assignee as the present application;

U.S. Pat. No. 6,092,526, entitled PERCUTANEOUS CHAMBER-TO-ARTERY BYPASS, filed on even date herewith and assigned to the same assignee as the present application;

U.S. Pat. No. 6,026,814, entitled SYSTEM AND METHOD FOR PERCUTANEOUS CORONARY ARTERY BYPASS, filed on Mar. 6, 1997 and assigned to the same assignee as the present application;

U.S. Pat. No. 6,035,856, entitled PERCUTANEOUS BYPASS WITH BRANCHING VESSEL, filed on Mar. 6, 1997 and assigned to the same assignee as the present application; and U.S. Pat. No. 6,155,264, entitled PERCUTANEOUS BYPASS BY TUNNELING THROUGH VESSEL WALL, filed on Mar. 6, 1997 and assigned to the same assignee as the present application.

BACKGROUND OF THE INVENTION

The present invention generally deals with vascular bypass methods. More specifically, the present invention deals with systems for performing percutaneous coronary artery bypass procedures.

Coronary arteries can become partially restricted (stenotic) or completely clogged (occluded) with plaque, thrombus, or the like. This reduces the efficiency of the heart, and can ultimately lead to a heart attack. Thus, a number of different systems and methods have been developed for treating stenotic or occluded coronary arteries.

Two methods which have been developed to treat occlusions and stenosis include balloon angioplasty and pharmacological treatment. However, where the occlusion is quite hard, it can be quite difficult, if not impossible, to cross the occlusion with an angioplasty device. In addition, some coronary stenosis are to diffuse to treat effectively with balloon angioplasty. Unfortunately, such occlusions are not readily susceptible to dissolution with chemicals either. In the past, patients with these types of occlusions have been candidates for open heart surgery to bypass the restrictions.

However, open heart surgery includes a myriad of disadvantages. Open heart surgery typically includes a great deal of postoperative pain. The pain is normally encountered because conventional open heart surgery requires that the sternum be cracked open, which is quite painful. Also, open heart surgery typically involves bypassing the occluded vessel, which, in turn, involves harvesting a vein from another part of the body for use as the bypass graft. One common source for the bypass graft is the saphenous vein which is removed from the leg. Harvesting the saphenous vein requires the surgeon to cut and peel the skin back from an area of the leg which is approximately 18 inches long and which extends upward to the groin area. This can be very traumatic and painful. Further, open heart surgery requires quite a lengthy recovery period which involves an increase hospital stay, and, consequently, greater expense.

Other than the pain and more lengthy hospital stay, open heart surgery involves other disadvantages as well. For example, during open heart surgery, it is common to cool the heart to a point where it stops. The blood from the remainder of the vasculature is then pumped through a pulmonary and cardiac bypass system. Any time the heart is stopped, there is a danger of encountering difficulty in restarting the heart (which is typically accomplished by warming the heart and massaging it). Further, even if the heart is restarted, it sometimes does not return to a correct rhythm. Also, open heart surgery can require the use of a device known as a left ventricular assist device (LVAD) to supplementarily pump blood to relieve the burden on the heart. This allows the heart to heal.

A significant reason that the heart is typically stopped during open heart surgery is that, if it were not stopped, the surgeon would be working in a dynamic environment. In such an environment, the target vessels and tissue to be treated are moving. Further, a system must be employed in such an environment to stop bleeding. Clinical studies indicate that, when blood flow is stopped using clamping devices and blood flow is diverted to a cardiac bypass system, a statistically significant instance of neurological problems caused by blood clotting results. The use of mechanical clamps to stop blood flow, and the use of a mechanical bypass system, results in an approximate six percent instance of neurological problems, such as stroke, memory failure, etc.

Given the difficulties of the techniques discussed above, another approach has been developed which does not require stoppage of the heart or an open chest during execution. This approach is to perform a bypass using a minimally invasive technique by entering the upper chest cavity, through a hole between ribs under visual observation. Such a technique is often referred to as minimally invasive direct coronary artery bypass (MIDCAB) (where the heart is not stopped), or heart port (where the heart is stopped). Such a system which is used to perform a bypass is disclosed in the Sterman et al. U.S. Pat. No. 5,452,733.

SUMMARY OF THE INVENTION

The present invention relates to a system for bypassing a restriction in a parent vessel of a mammal via a venous vessel. In the system of the present invention, an adjacent venous vessel is fluidly coupled to a restricted artery distal of a restriction to provide blood flow through the artery distal of the restriction via the venous vessel.

It should be noted that the drawings are not necessarily drawn to scale and certain portions have been exaggerated for clarity.

DETAILED DESCRIPTION OF THE PREFERRED EMBODIMENTS

Figure 1:
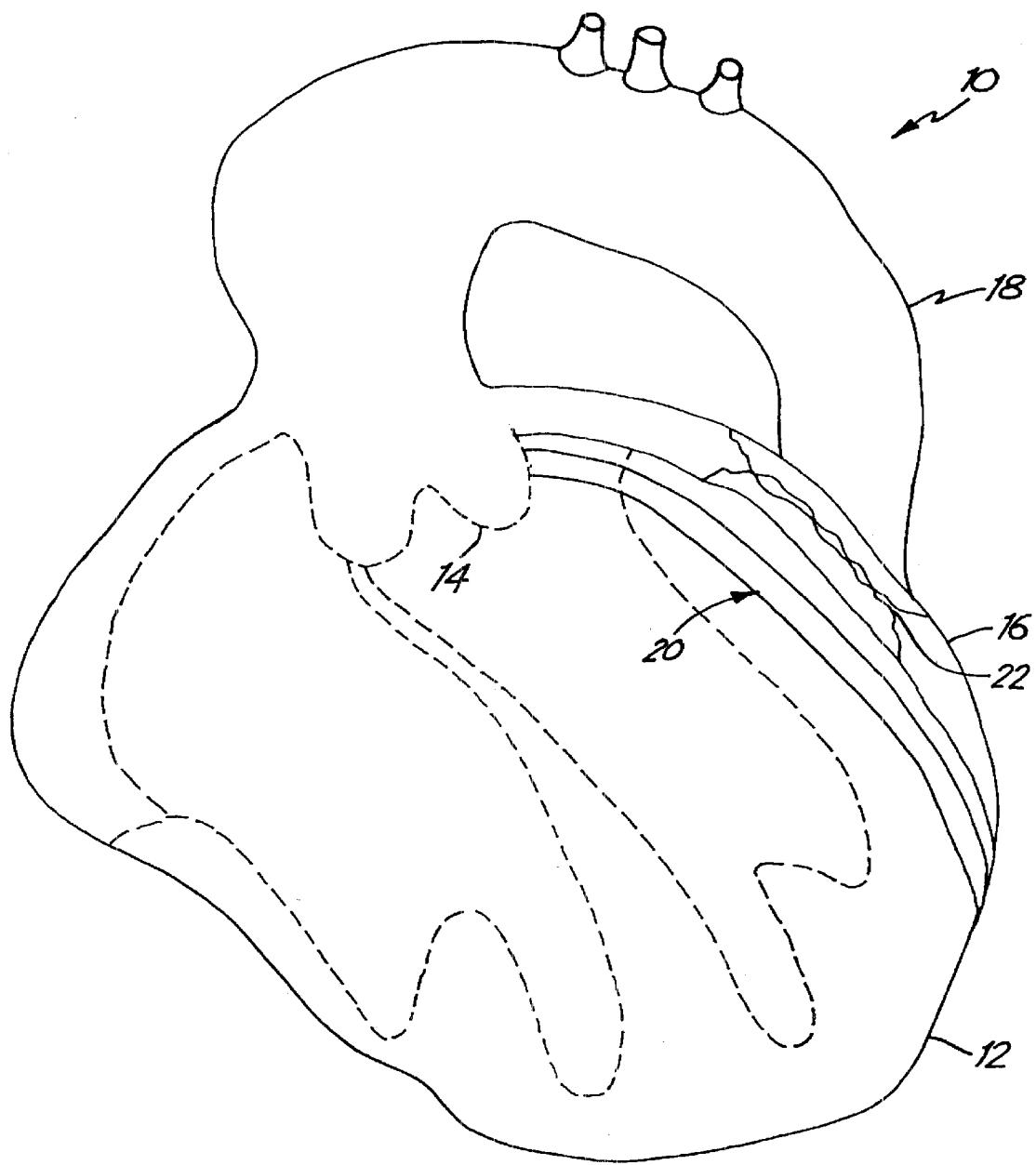
FIG. 1 illustrates a portion of a coronary vascular system with an artery having a restriction.

FIG. 1 illustrates a portion of a vascular system 10. System 10 includes heart 12, heart valve 14, coronary artery 16, aorta 18 and coronary vein 20. Coronary artery 16 includes restriction 22. Veins 20 are arranged adjacent to coronary arteries 16. Coronary arteries 16 carry oxygenated blood to the heart tissue, while veins 20 carry blood which is charged with carbon dioxide back to the heart chambers for subsequent delivery to the lungs via the pulmonary artery.

While restriction 22 is shown in FIG. 1 as being a total occlusion, restriction 22 can be any disease including complete occlusion, or simply a stenotic lesion. Since artery 16 is occluded oxygenated blood flow therethrough is restricted. The present invention relates to a bypass system for bypassing the restriction 22 in artery 16 by using vein 20 as a means for providing blood flow past the restriction 22 in artery 16.

Figure 2:
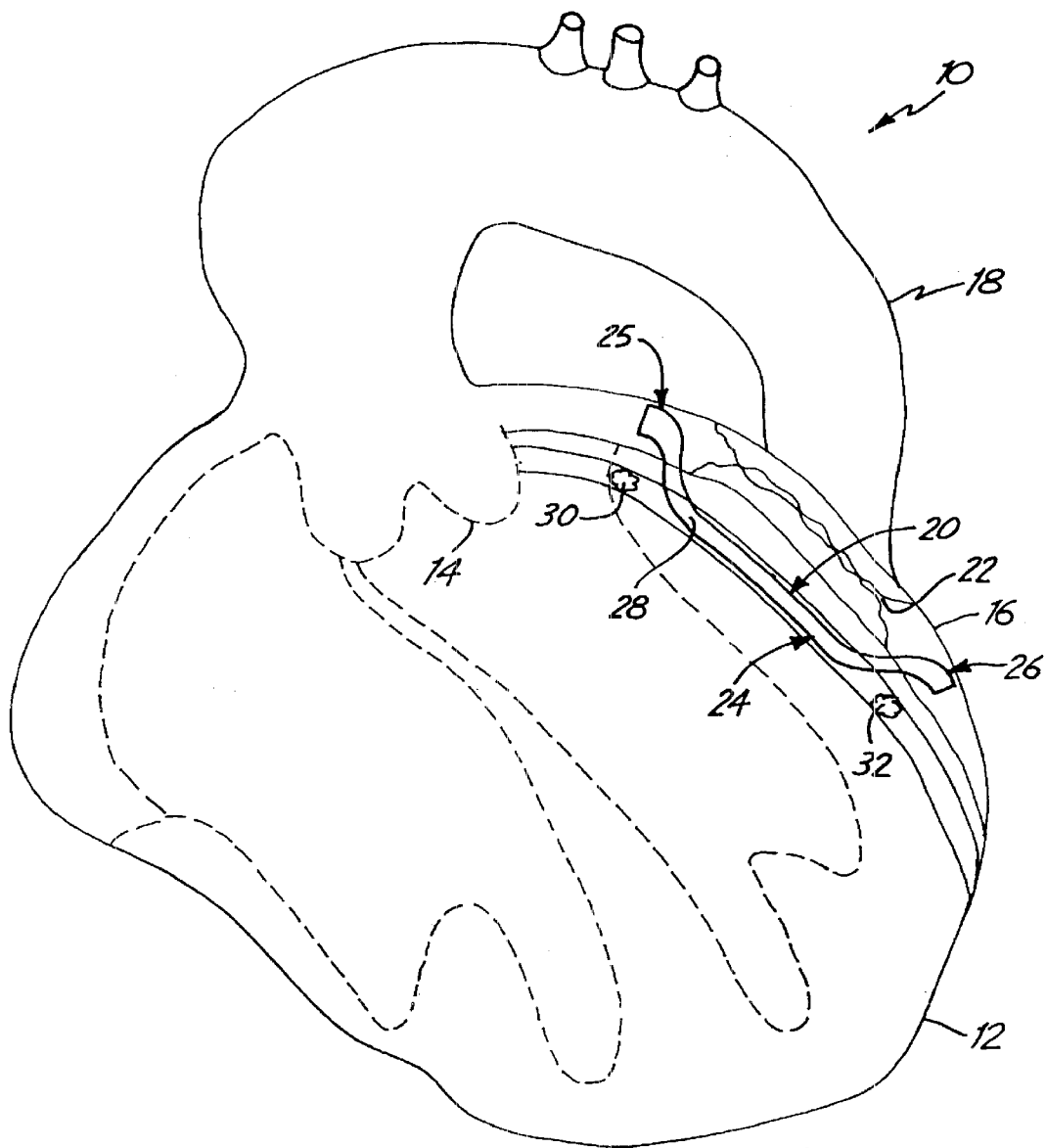
FIG. 2 illustrates an embodiment of a bypass system of the present invention for bypassing a restriction in an artery.

FIG. 2 illustrates one embodiment of the bypass system of the present invention. In the embodiment shown in FIG. 2, a bypass conduit 24 extends through a portion of vein 20 to couple a portion of the coronary artery 16 proximal to the restriction 22 to another portion of the coronary artery 16 distal of the restriction 22. The bypass conduit 24 includes opposed ends 25 and 26, and an inner lumen 28. Ends 25 and 26 are secured to an inner wall of the coronary artery 16 proximal and distal of the restriction 22, respectively. Blood flows from the coronary artery 16 through lumen 28 back into the coronary artery 16 to bypass restriction 22 in artery 16.

In one embodiment of the present invention, vein 20 includes proximal and distal occlusions 30 and 32 for restricting the flow of blood through vein 20. The proximal and distal occlusions 30 and 32 may provide a total occlusion for blood flowing through vein 20, may be designed to partially occlude blood flow so that blood can continue to flow through vein 20, may be only temporary occlusions, or may be eliminated. In the embodiments in which flow is maintained through vein 20, the diameter of the bypass conduit 24 is sized smaller than the diameter of the vein 20 to provide area for blood to flow through vein 20 past the bypass conduit 24.

Figure 3:
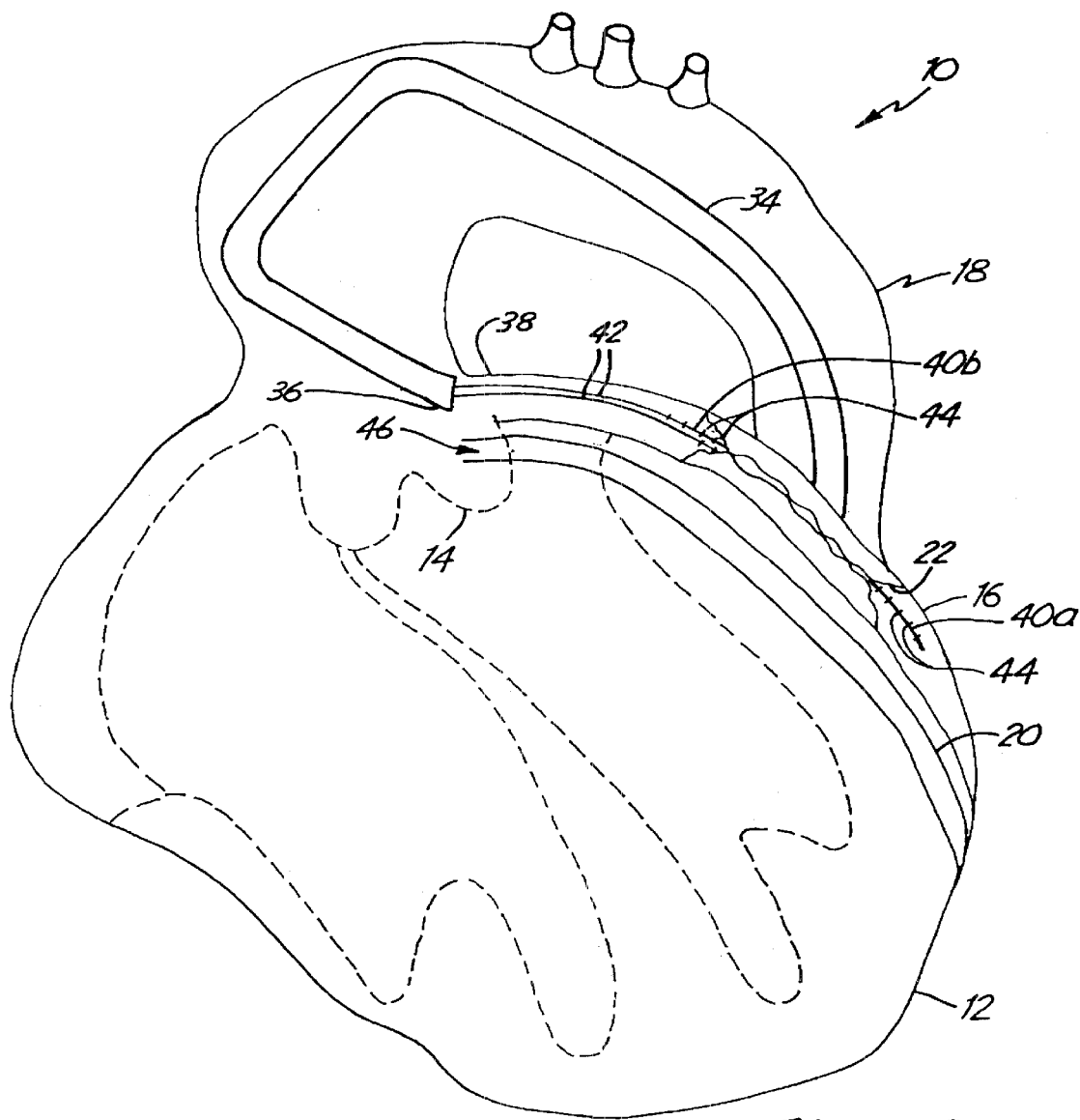
FIG. 3 illustrates insertion of a guide device into the vascular system for performing a bypass according to the present invention.

FIG. 3 illustrates a first portion of a procedure for deploying one preferred embodiment of the bypass system of the present invention. As illustrated in FIG. 3, a standard guide catheter 34 is first advanced through aorta 18 (preferably initially through a femoral artery and then through the systemic vasculature up to, and through, aorta 18). In a preferred embodiment, a distal end 36 of guide catheter 34 is positioned proximate an ostium 38 of artery 16.

Guide devices 40a and 40b are inserted through the guide catheter 34 into coronary artery 16 to locate the restriction 22 for performing the bypass of the present invention. Guide device 40a locates a distal end of the restriction 22, and guide device 40b locates a proximal end of the restriction 22. The guide devices 40a and 40b locate the restriction 22 for positioning occlusions 30 and 32 in vein 20 and for subsequent steps as are described in greater detail below. Preferably, guide devices 40a and 40b each include an elongated wire 42 and locating members 44 at the distal end of the wire 42. Guide device 40a is inserted through the coronary artery 16 and across the restriction 22 to position member 44 distal of the restriction 22. Guide device 40b is inserted through the coronary artery 16 to the restriction 22 to position member 44 proximal of the restriction 22. Preferably, radiopaque dye or contrast fluid is inserted into artery 16 and for locating restriction 22 and positioning the guide devices 40 and 40b.

Alternatively, a single guide device may be employed with multiple locating members 44 for locating the proximal and distal positions of the restriction 22. If a single guide device is employed, then the multiple locating members 44 must be spaced to locate both the proximal and distal sites of the restriction 22. The extent between the proximal and distal sites of the restriction may be observed by inserting radiopaque dye or contrast fluid into artery 16. In one embodiment of the invention, the locating members 44 may be radiopaque markers. Alternatively, the guide device may include a conductive wire or fiber having a plurality of sensors or receivers at a distal end of the wire as will be explained.

Figure 4A:
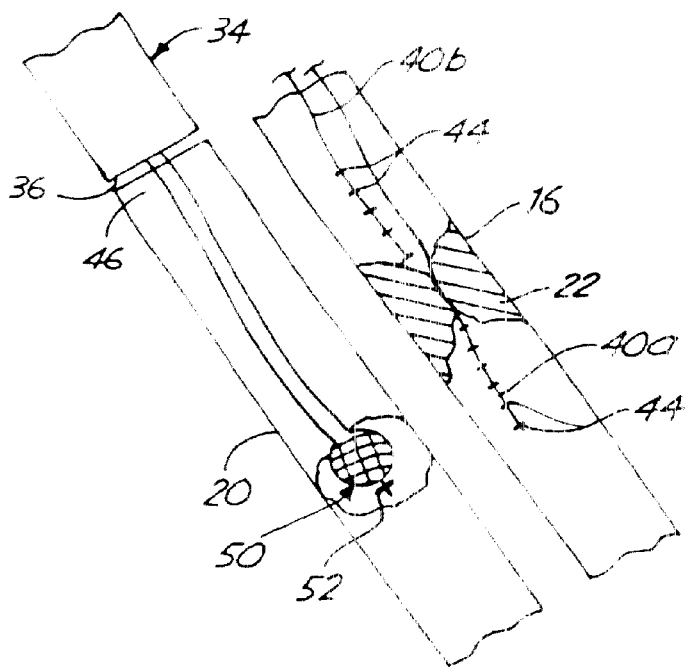
FIGS. 4A–4B illustrate formation of occlusions in a venous vessel according to an embodiment of the bypass system of the present invention.
Figure 4B:
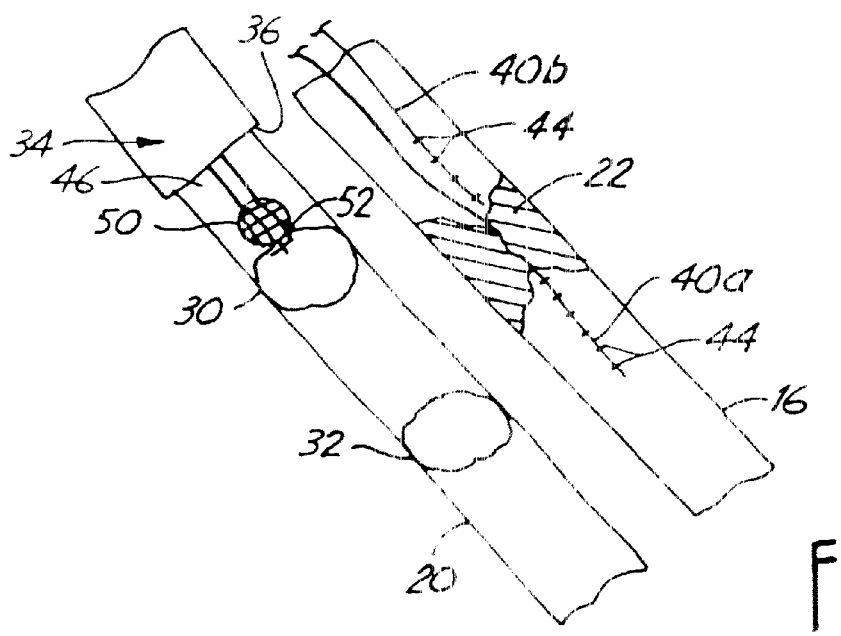

Thereafter, as illustrated in FIGS. 4A–4B, the guide catheter 34, or another suitable catheter or conduit, is orientated within a coronary sinus to align a distal end 36 of the catheter with an ostium 46 of the vein 20 for advancing an occlusion forming device 50 into the vein 20. The occlusion forming device 50 is advanced through the vein 20 to form proximal and distal occlusions 30 and 32, proximal and distal of the restriction 22, as illustrated in FIGS. 4A–4B. As illustrated in FIG. 4A, first the device 50 is advanced through the vein 20 to align the device 50 distal of the restriction 22 to form the distal occlusion 32. Thereafter, the occlusion forming device 50 is withdrawn proximally and aligned proximal to restriction 22 to form proximal occlusion 30.

The occlusion sites are located in cooperation with the guide devices 40 inserted into artery 16 for identifying the position of the restrictions 22. Preferably, a distal end of the occlusion forming device 50 includes locating member 52 for locating the distal end of the device 50 relative to restriction 22. In particular, locating member 52 is aligned with (or advanced distally relative to) locating member 44 of guide device 40a in artery 16 to locate device 50 proximal of restriction 22 during formation of occlusion 32. Locating member 52 is then aligned with (or moved proximal relative to) locating member 44 of guide device 42b during formation of occlusion 30. As previously explained, locating members 52 and 44 may be radiopaque markers so that device 50 is moved under fluoroscopic observation for aligning the device 50 to form occlusions 30 and 32. Alternative to radiopaque markers, various transmitters may be included on the device 50 for cooperation with sensors or receivers on guide devices 40a and 40b.

Preferably, the occlusion forming device 50 is simply a delivery catheter which is used to deliver coils, collagen, or another suitable material. As previously explained, the occlusion forming device 50 may be designed to form a complete occlusion so that blood flow through the vessel 20 is completely arrested or a partial occlusion to provide limited blood flow through vessel 20. Occlusion forming device 50 may also be a balloon catheter or a plurality of balloon catheters for forming temporary occlusions. In that case, one balloon is preferably positioned and inflated to form occlusion 30, and another balloon is positioned and inflated to form occlusion 32. After occlusions 30 and 32 are formed, the occlusion forming device 50 may preferably be withdrawn from the system 10 through guide catheter 34.

Prior to proceeding with the method illustrated herein, the patient may be placed on full cardiopulmonary bypass and heart 12 is stopped. Alternatively, the heart need not be stopped if temporary occlusion devices are deployed in the artery 16 and vein 20 to stop blood flow in the relevant vasculature when incisions are made through the vascular walls. FIGS. 5A–5E illustrate a temporary occlusion device 70 having an elongated member 72, an inflation lumen 74 and proximal and distal balloons 76 and 78 (shown deflated in FIG. 5A). If vein 20 is not totally occluded by permanent occlusions 30 and 32, a similar occluding device can be employed in vein 20 during the incision process.

The balloons 76 and 78 are spaced to be positioned proximal and distal of the incisions. In particular, balloon 76 is positioned proximal of the restriction 22 and of a proximal incision site and balloon 78 is positioned distal of the restriction 22 and of a distal incision site. The balloons 76 and 78 are retained in an expanded position during the cutting procedure, as illustrated later with respect to FIG. 5B. This serves to occlude vessel 16 after it has been severed. As shown, the occluding device 70 can be the same as the guide device 40 or may be a separate instrument independently inserted. Other systems and methods to halt blood flow when vessels are severed can also be used. However, occluding balloons have a relatively low instance of emboli formation, and therefore have a lower instance of neurological problems which result from the formation of emboli than do other types of systems used to arrest blood flow.

Figure 5A:
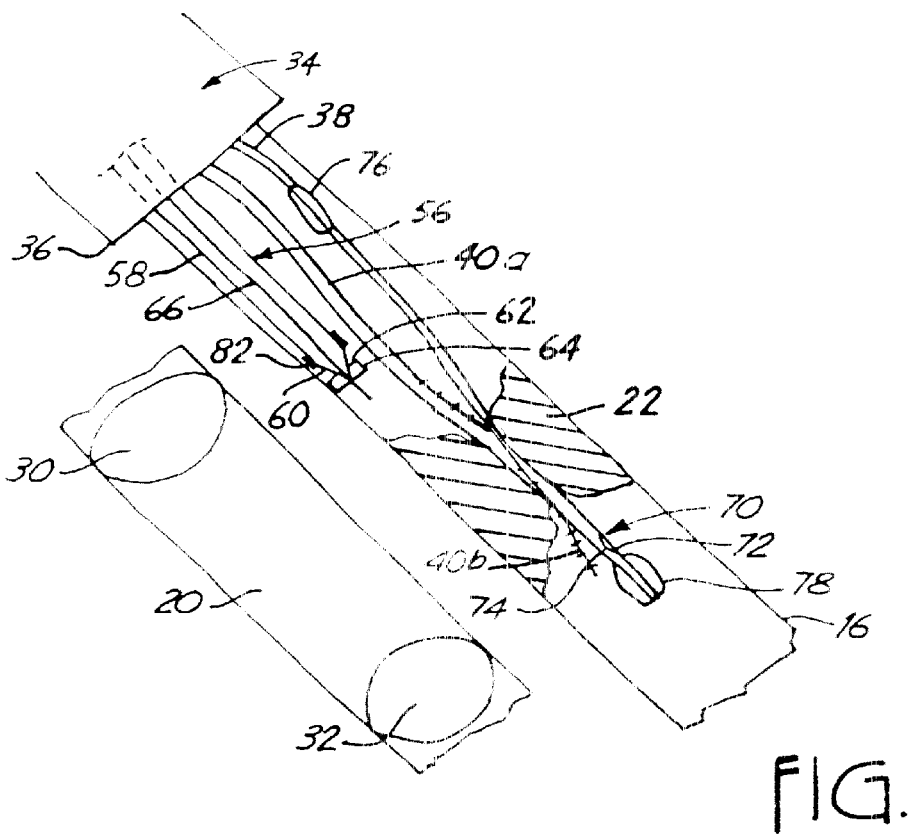
FIGS. 5A–5E illustrate insertion of a cutting device into the vascular system for performing a bypass according to an embodiment of the present invention.
Figure 5B:
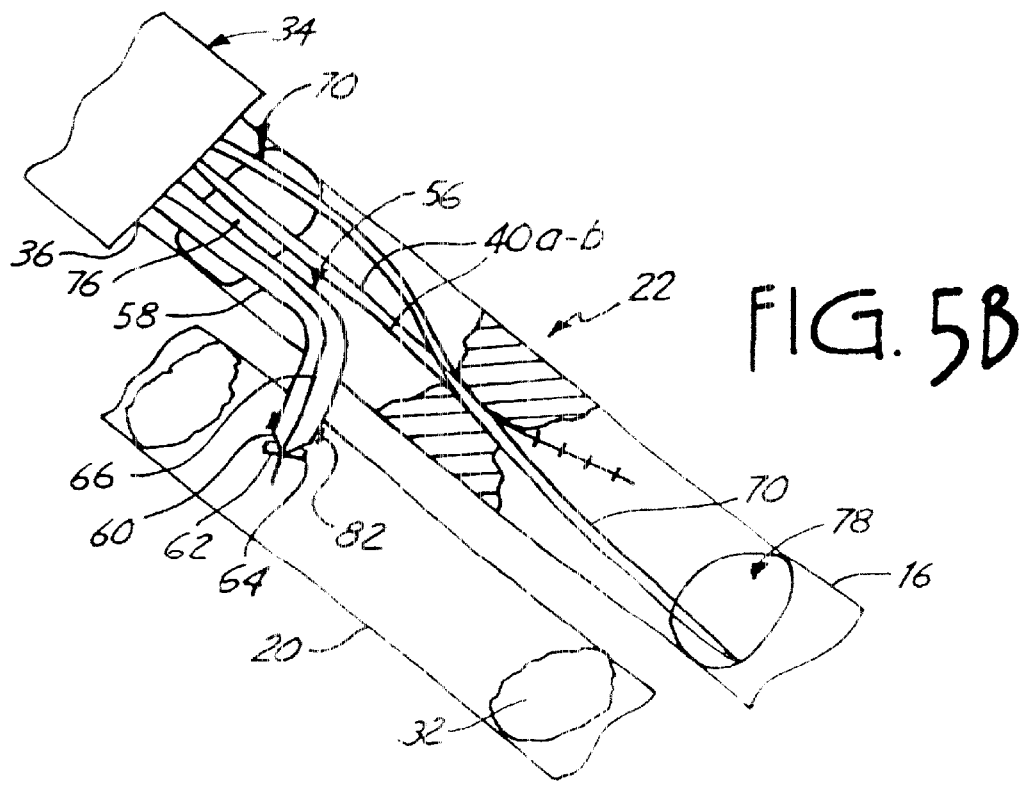
Figure 5C:
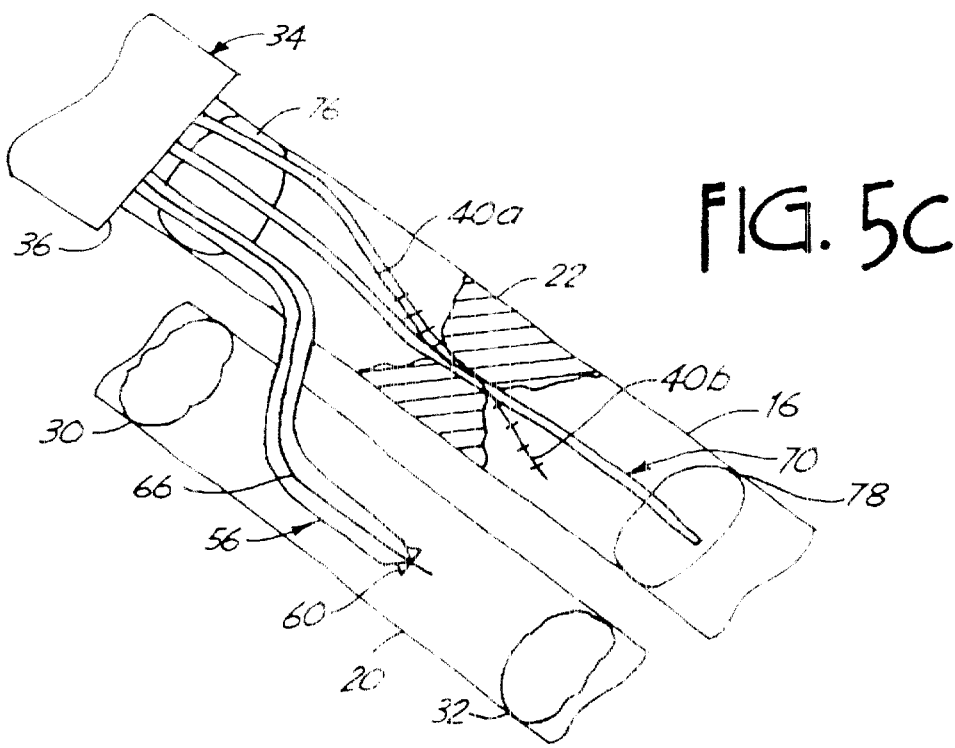
Figure 5D:
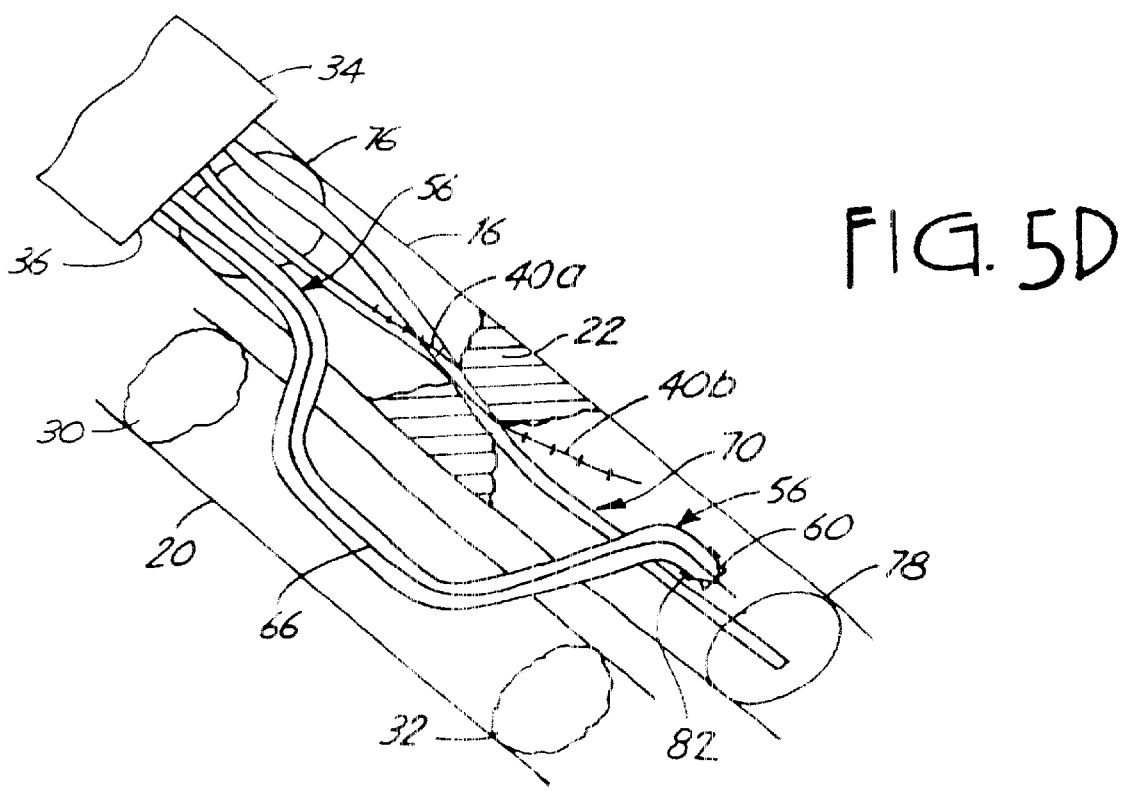

FIGS. 5A–5C illustrates the next steps for bypassing restriction 22 in accordance with a preferred embodiment of the present invention. As shown in FIG. 5A, a cutting device 56 is inserted into artery 16 through guide catheter 34 by aligning the distal end 36 of the guide catheter 34 with the ostium 38 of artery 16. Cutting device 56 is used to cut through the arterial wall and vein wall for connecting artery 16 and vein 20 proximal and distal of the restriction 22.

The cutting device 56 is first inserted through artery 16 and advanced to the restriction 22 as shown in FIG. 5A. Preferably, the cutting device 56 includes an elongate portion 58, and a distal tip 60, which includes a cutting needle 62 and a dilator sheath 64. The elongate portion 58 includes a lumen for advancing the cutting device over a guide wire 66 inserted into the restricted artery via guide catheter 34. Needle 62 is used to make an incision, or aperture in the walls of vessels 16 and 20. Dilator sheath 64 is then advanced through the incision to open the incision for insertion of instruments therethrough.

As progressively illustrated in FIGS. 5A–5E, the distal end 60 of the cutting device 56 is steered through the first incision made in the artery wall and vein wall proximal of the restriction 22. Balloon 76 and restriction 22 occlude vessel 16 at the first incision site. Occlusions 30 and 32 occlude vein 20 at the first incision site. The cutting device 56 is advanced through vein 20 to a position distal of restriction 22 in artery 20. Thereafter, a second incision is cut in the vein 20 and artery 16 distal of the restriction 22. Balloon 78 and restriction 22 occlude vessel 16 at the second incision site. Occlusions 30 and 32 occlude vessel 20 at the second incision site. The cutting blade can be supported by an articulated catheter or elongate member so that it can be rotated by manipulation of the physician, in order to position the blade to cut through the vessel walls at the desired orientation.

Locating techniques are used to position the cutting device 56 to make incisions in the arterial and venous walls proximal to and distal to restriction 22. As previously explained, guide devices 40a and 40b are initially inserted in artery for locating restriction 22. The guide devices 40a and 40b may be formed of a conductive wire or fiber, which includes a plurality of sensors or locating members 44. The distal end of cutting device 56 is preferably provided with one or more locating members 82, such as a transmitter. In one preferred embodiment, transmitter 82 may include an ultrasound transmitter, radiofrequency transmitter, a plurality of point light sources, a single intense point light source, or an electromagnetic transmitter (such as where current is actively applied to a coil to induce a magnetic field thereabout). Locating members 44 are suitable devices, such as sensors or receivers, which are compatible with transmitter 82 to receive or sense the signals provided by transmitter 82.

For instance, where transmitter 82 includes an inductive magnetic coil, receivers 44 form a magnetic sensor array to receive the signals induced in the coil. When transmitter 82 includes an ultrasound transmitter, receivers 44 form an ultrasound imager so that the relative positioning of receivers 44 and transmitter 82 can be determined by the physician. When transmitter 82 includes a single point light source, or an array of point light sources, receivers 44 are formed as an imaging fiber optic bundle which detect the light emitted by the light source or light sources forming transmitter 82. In addition, when transmitter 82 includes an RF transmitter, for example, receivers 44 are formed as a directional antenna. In any of the above cases, or similar cases, the relative position between transmitter 82 and receivers 44 can be determined for locating the cutting positions for the vein 20 and artery 16. It should be noted that the transmitter 82 can alternatively be located in the artery and the cutting device 56 may include receivers.

In another preferred embodiment, location of various items within the vasculature is accomplished using a triangulation and coordinate mapping system. In that embodiment, a radio frequency (RF) emitter is placed in the heart, or in the vasculature near the heart. The RF emitter is preferably placed on a catheter or another device, the placement of which must be guided. A number of reference electrodes (or receivers) are placed on the outside of the body at various points on the chest and back. In the preferred embodiment, three reference receivers are placed on the exterior of the body, two on the chest on opposite sides of the heart and one on the back. The three receivers are used to triangulate on the RF transmitter located on the device within the vasculature. Three dimensional modeling can be used, along with known motion and analysis techniques to determine the placement and motion of the RF transmitter within the vasculature. Such a system can be used to obtain true position and the relative positions of different objects in the vasculature. Of course, a higher frequency signal could also be used, and a similar device could be used in which magnetic sensing devices are employed.

Figure 5E:
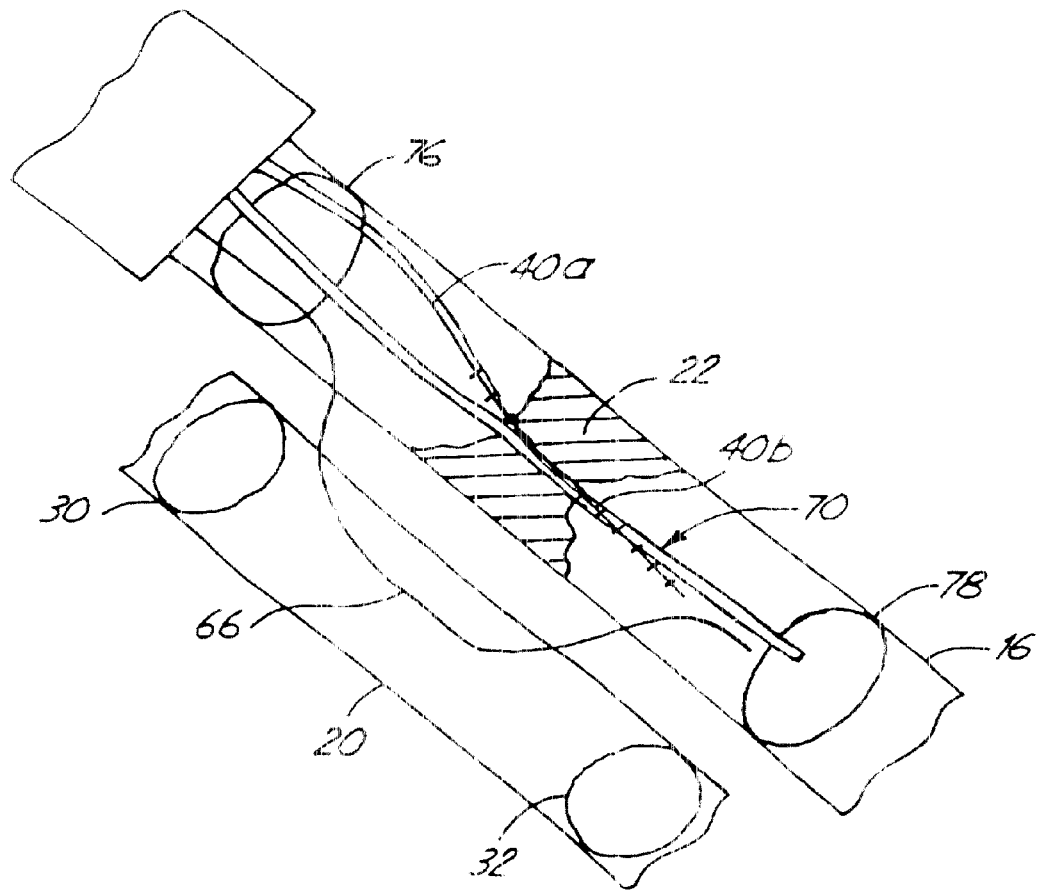

Thus, as described, the first incision position proximal to the restriction is located in the artery 16 via the transmitter 82 on the cutting device 56 and sensors 44 on the guide device 40a. The first incision position of the venous vessel is located via transmitter 82 on the cutting device 56 and a locating device (not shown) inserted into the venous vessel. The second incision positioned in the vein 20 and artery 16 distal to the restriction 22 are located via the transmitter 82 on the cutting device 56 and sensors 44 on the guide device 40b. After the cutting device 56 has cut incisions in the artery and vein both proximal and distal of the restriction 22, the cutting device 56 is withdrawn as illustrated in FIG. 5E, preferably leaving wire 66 in place. While the cutting device 56 is withdrawn, the inflated balloon 76 is either momentarily deflated to allow the cutting device 56 to be withdrawn or the balloon 76 is formed such that it need not be deflated at all. For instance, balloon 76 may be formed with a passage therethrough which supports a guiding type catheter through which the cutting device 56 and any other suitable devices are passed. In that case, the devices can be advanced through the guiding type catheter (and hence through balloon 76) without deflating balloon 76.

Figure 6A:
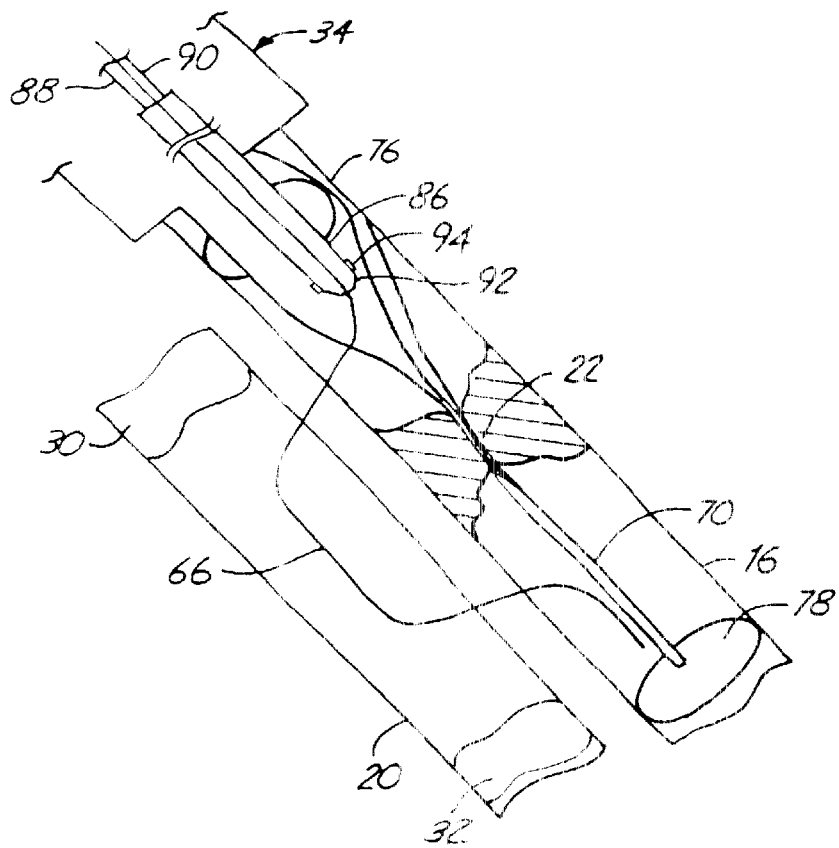
FIGS. 6A–6E illustrate insertion of a graft for performing a bypass according to an embodiment of the present invention.
Figure 6B:
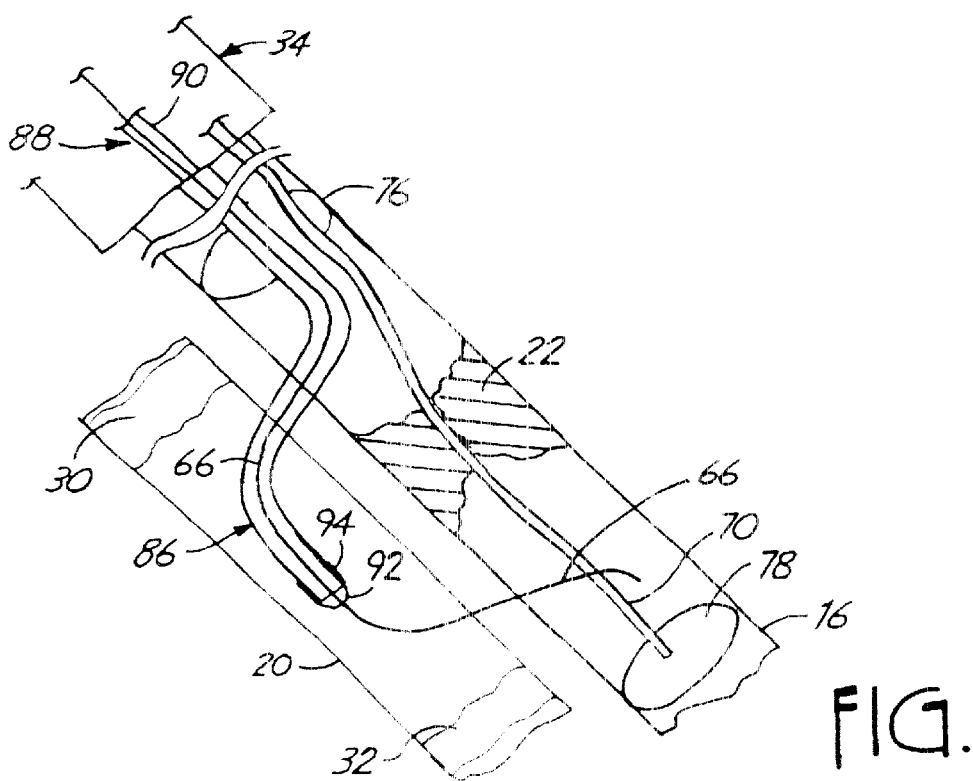
Figure 6C:
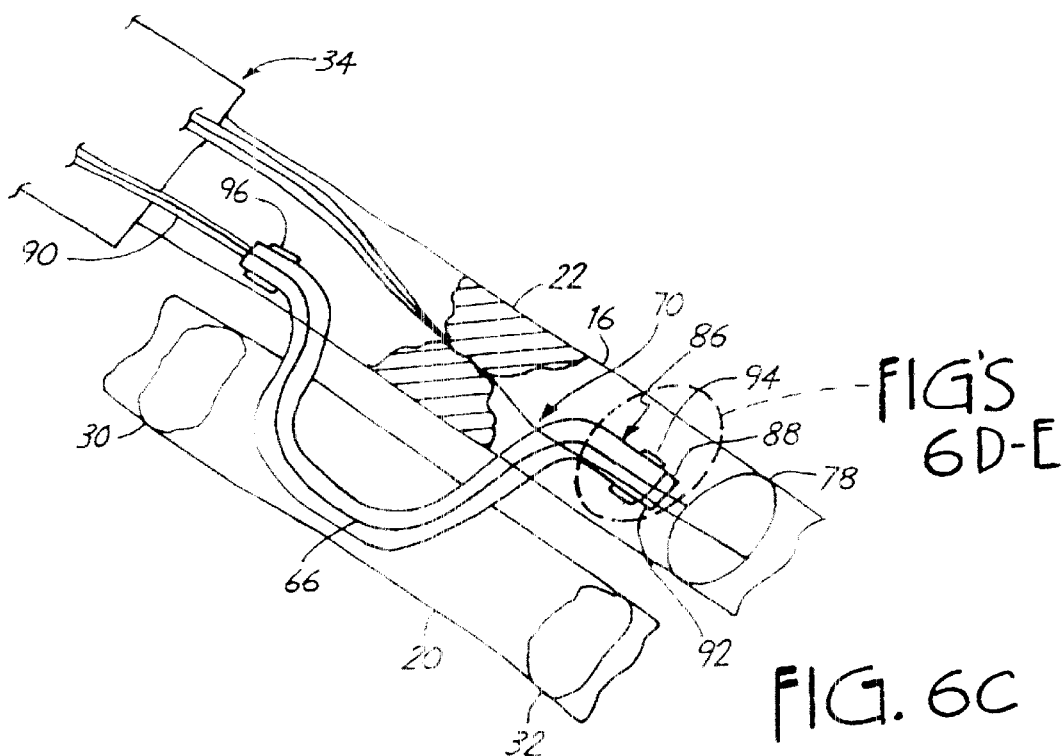

In any case, a shunting graft 86 is then inserted as shown in FIG. 6A–6D. Alternatively, graft 86 can be inserted concurrently with the cutting device 56. The shunting graft 86 is inserted via an introducer 88 which is advanced over guide wire 66. The length of the graft 86 is preferably determined based upon a pre-procedure analysis of the restriction, via fluoroscopy or other means. A distal end of the graft 86 is removably secured to the introducer 88 and moveable therewith for insertion of graft 86. Introducer 88 includes an elongated element 90, including a lumen for advancement over guide wire 66 and a tip 92. Introducer 88 and graft 86 are advanced through vessels 16 and 20 via guide wire 66 to position graft 86 as shown in FIG. 6C. The introducer 88 may include a locating device of the type previously described for locating the graft relative to guide devices 40a and 40b.

In a preferred embodiment, a body of the graft 86 is preferably either a biologically compatible, artificial graft (such as PTFE material), or a section of a human vein, such as a saphenous vein graft. The graft 86 includes a pair of stents 94 and 96 at opposed ends for forming an anastomosis. Stents 94 and 96 are preferably formed of an expandable, woven, braided, or mesh material which can be selectively expanded to have a preselected or variable outer diameter which approximates the inner diameter of the vessel or aperture within which it is deployed.

The ends of graft 86 are preferably attached to either the inner or outer surfaces of stents 94 and 96. The connections between the stents 94 and 96 and the graft 86 can be accomplished in any number of suitable ways, such as through the use of an appropriate adhesive, such as weaving the stent directly into the graft material, such as by forming a frictional fit therebetween, or by utilizing another suitable connection mechanism as will be explained herein.

Figure 6D:
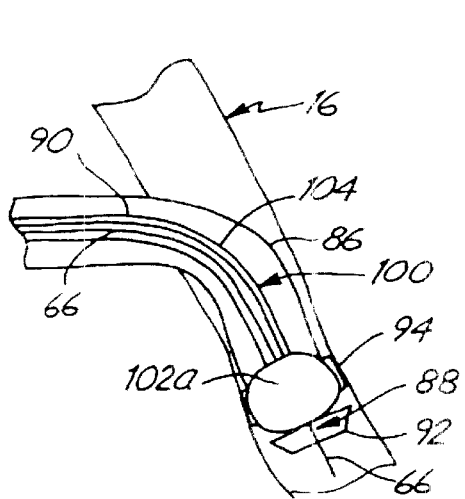
Figure 6E:
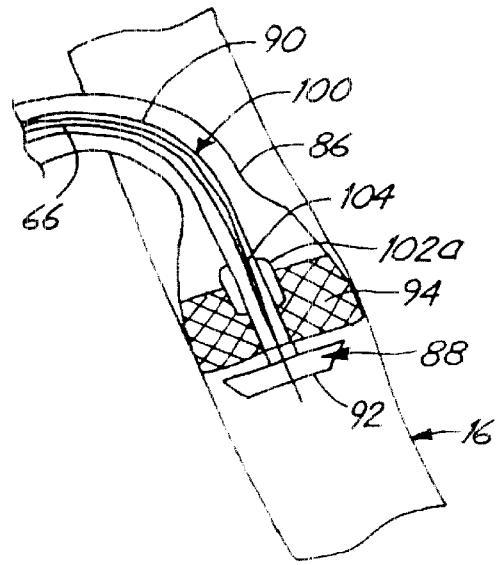

Stents 94 and 96 are deployed to secure opposed ends of graft 86 to the artery wall. FIGS. 6D–6E are detailed views illustrating deployment of stent 94. In one preferred embodiment, a balloon catheter system 100 is used to deploy stents 94 and 96. As illustrated in FIGS. 6D–6E, in one embodiment, the balloon catheter system 100 is integrally formed with the introducer 88 and is insertable therewith. The balloon catheter system 100 includes balloon 102 and a proximal balloon (which is not shown, and which deploys distal stent 96) and an inflation lumen 104. The balloons are placed such that, when properly deployed or expanded, distal balloon 102 lies within the interior of stent 94 and the proximal balloon (not shown) lies within the interior of stent 96. Alternatively, the balloon catheter system 100 can be formed independently of introducer 88, or separate balloon catheter systems 100 may be used to deploy proximal and distal stents 96 and 94.

Once in place, the proximal and distal balloons are expanded. FIG. 6D illustrates distal balloon expanded to deploy or expand stent 94. The balloons are first inflated to expand stents 94 and 96 to low pressure. The balloons are then expanded to such a degree that stents 94 and 96 expand radially outwardly so that the exterior of the stents 94 and 96 achieves an outer diameter which closely approximates the inner diameter of the vessel within which it is deployed. This causes a frictional fit between the outer surface of the stents 94 and 96 (or the ends of graft 86) and the inner surface of the lumens within which they are deployed.

In addition, a suitable adhesive or glue can be applied to the stents 94 and 96 to further facilitate anastomosis in the vessels in which they are deployed. Alternatively, intraluminal suturing may be used to secure the stents 94 and 96 to the arterial wall. Intraluminal suturing is described in greater detail in the following U.S. Pat. No. 5,080,663 entitled SEWING DEVICE; U.S. Pat. No. 5,364,389 entitled METHOD AND APPARATUS FOR SEALING AND/OR GRASPING LUMINAL TISSUE; U.S. Pat. No. 5,545,171 entitled ANASTOMOSIS CATHETER; and U.S. Pat. No. 5,591,179 entitled ANASTOMOSIS SUTURING DEVICE AND METHOD and, which are hereby incorporated by reference. Alternatively, mechanical hooks or metal clamps may be used to secure stents 94 and 96 within artery 16.

Deployment of stents 94 and 96 releases graft 86 from introducer 88 so that the introducer 88 may be withdrawn. After the stents 94 and 96 are deployed and secured to the artery wall proximal and distal of the restriction 22, balloons 102 are deflated as illustrated in FIG. 6E and the balloon catheter system 100 and introducer 88 are withdrawn from the patient through the guide catheter 34 and the anchored graft 86 remains in place. Thereafter, guide wire 66, guide devices 40a and 40b, and occluding device 70 are withdrawn from the patient via guide catheter 34. Also, if occlusions 30 and 32 are temporary, any temporary occlusion system can then be removed. Thereafter, guide catheter 34 is removed.

Figure 7A:
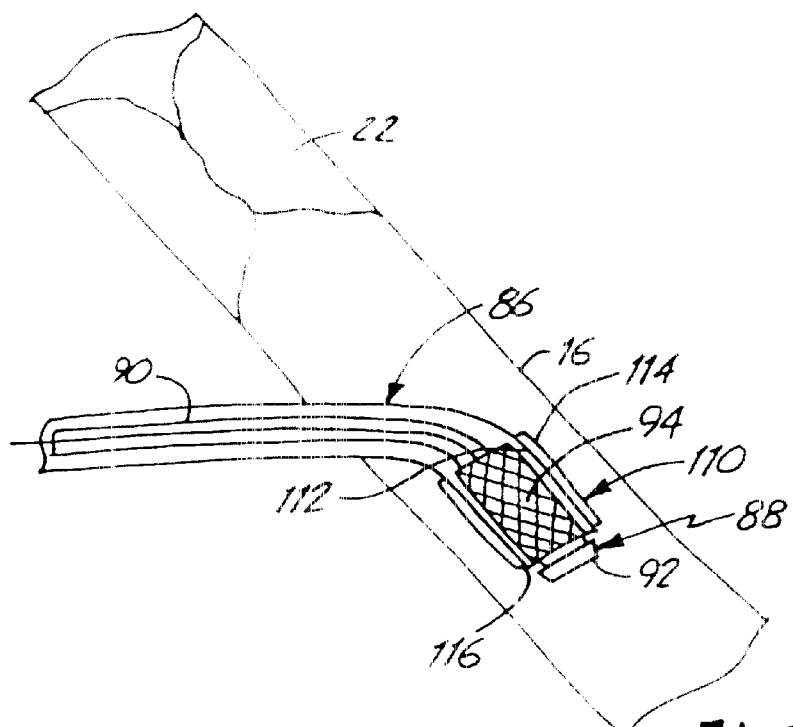
FIGS. 7A–7B illustrate an embodiment of a graft for providing a bypass conduit in accordance with an embodiment of the present invention.
Figure 7B:
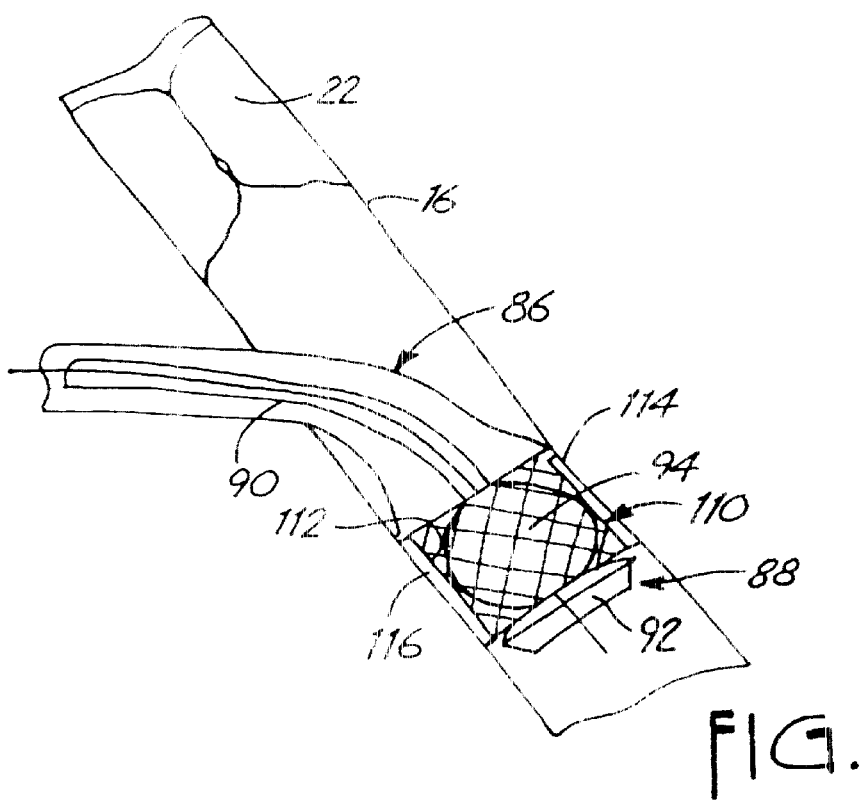

In another embodiment of graft 86 as illustrated in FIGS. 7A–7B, ends of graft 86 include sheath 110. Stents 94 and 96 (stent 96 not shown in FIGS. 7A–7B) are each coupled to graft 86 via a sheath 110. Sheath(s) 110 includes an inner surface 112, an outer surface 114 and a central portion 116 between the inner and outer surfaces 112 and 114. Preferably, inner surface 112 is impermeable to fluid flow, and outer surface 114 when rendered discontinuous or broken, is permeable to fluid flow. Central portion 116 between inner surface 112 and outer surface 114 contains either a substance suitable to enhance anastomosis at that site, or another suitable drug.

Once ends of graft 86 are suitably located in vessel 16, as illustrated in FIG. 7A, a balloon, similar to that previously described, is inflated in the interior of stents 94 and 96 to deploy stents 94 and 96. Thus, the sheath 110 expands radially outwardly such that the outer diameter of sheath 110 expands to a sufficient extent that it approximates the inner diameter of vessel 16, the outer surface 114 is preferably rendered discontinuous (or broken) to release the substance carried by intermediate region 116 of sheath 110.

In one preferred embodiment, the substance contained by region 116 of sheath 110 includes an adhesive which immediately sets or cures with the passage of time once stents 96 and 94 are deployed in vessel 16 to enhance anchoring ends of graft 86 within vessel 16. Suitable adhesives are preferably bioadhesives such as fibrin glues commercially available under the tradenames Tisseel or Tissucol from Immuno, AG of Vienna, Austria; cyanacryolates commercially available under the tradenames Histoacryl, Bucrylate or Hexacryl; or Gelatin-Rocorcinol, formaldehyde, or mussel adhesive protein. In another preferred embodiment, growth factors or other biological substances are contained within sheath 110 which also enhance an anastomosis and healing in that region.

It has also been found that some grafts tend to degenerate after approximately 10 years of use. Therefore, in accordance with one additional aspect of the present invention, the grafts are structurally reinforced with a mechanical outer shell to strengthen the graft. In one embodiment, the mechanical outer shell is a sheath which is formed of, for example, woven Dacron, Gortex, or polyester. The sheath is preferably configured so that the vein graft can be passed through the sheath prior to deployment of the graft in the vasculature. Then, the reinforcing sheath is pulled at its opposite ends, in longitudinally opposing directions. This causes the woven sheath to tighten down around the outer surface of the vein graft and thereby reinforce the vein graft.

In another embodiment, the vein graft is wrapped with a material which strengthens the vein graft. In one embodiment, the vein graft is wrapped with, for example, hook and loop tape (such as Velcro tape) wherein the hooks on the hook and loop tape engage the adventitious layer of the vein graft. The hook and loop tape can be any suitable fabric backed microhoop strip which has hooks suitable for engaging the adventitious layer on the exterior of the vessel wall. Ultrasound is preferably used to measure the size of the vein and to adjust the tension in the reinforcement layer such that the interior of the reinforcement layer closely approximates the exterior dimension of the vein graft.

As previously explained, graft 86 may be a human vein, such as a saphenous vein graft or another type of graft. FIGS. 8–11 illustrate alternate embodiments of a system for attaching vein graft 86 to vessel 16 and/or vessel 20. The system involves fusing the vein graft 86 to the receiving vessel, such as vessel 16, by heating adjacent boundary layers of the vein graft 86 and vessel 16 via an inductive heat source.

Figure 8:
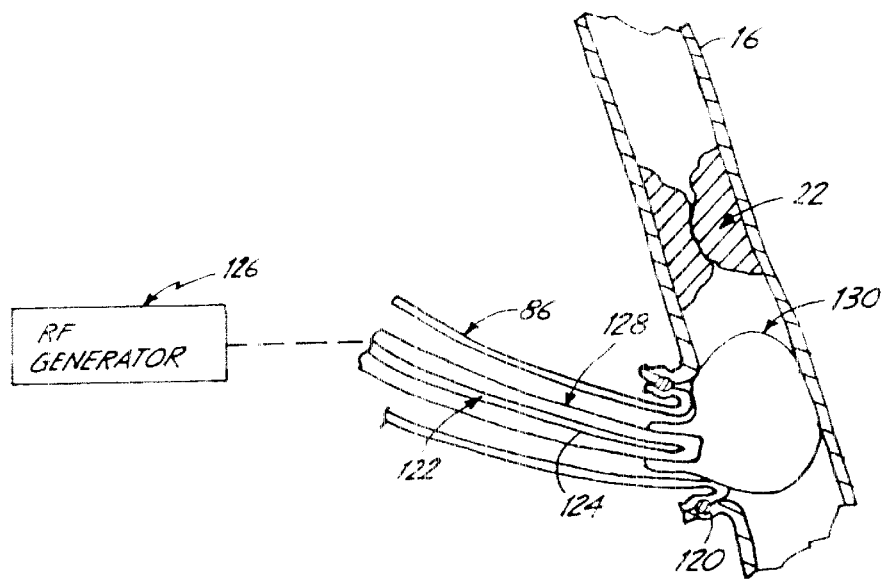
FIG. 8 illustrates a system for fusing a vessel graft to a restricted artery.

As shown in FIG. 8, the incision formed in vessel 16 by a cutting device includes an opened flap formed by a cut portion of the vessel wall. Ends of the vein graft 86 include a steel ring 120 disposed about the outer perimeter of an attachment portion of the vein graft 86. Vein graft 86 is inserted through vessel 16 to align the ends of the vein graft 86 with the opened flap of vessel 16. An inductive heating device 122 is positioned relative to graft 86 to induce current in rings 120 at the end of the vein graft 86 to heat ring 120 to fuse graft 86 and vessel 16. The inductive heating device preferably includes an inductive coil 124 coupled to an RF generator 126. The coil 124 is aligned with rings 120 and RF energy is supplied to coil 124 to induce a current in rings 120 to heat the boundary layers of graft 86 and vessel 16 to fuse graft 86 and vessel 16.

A catheter device 128 is used to facilitate insertion and positioning of the proximal and distal ends of the vein graft relative to the vascular region to be treated. The catheter device 128 preferably includes a balloon 130 which is inflated to secure the end of the vein graft 86 relative to the incision flap in vessel 16. Heating coil 124 may be inserted with catheter device 128 or separately inserted from catheter device 128 and graft 86. The distal end of the vein graft 86 may be coupled to catheter device 128 for insertion similar to introducers previously described. Ring 120 is permanently implanted and premounted on graft 86 for fusing and is formed of a biocompatible material. Preferably, ring 120 is formed of a solid stainless steel material to induce a current for fusing.

Figure 9:
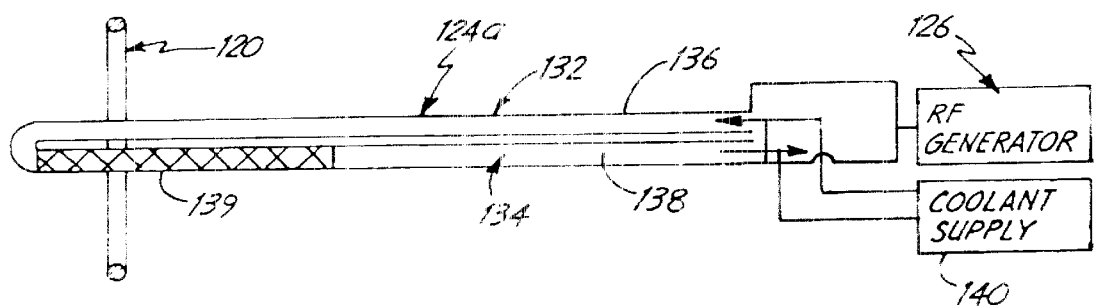
FIGS. 9–10 illustrate embodiments of an inductive coil for heating a ring for fusing a vessel graft to a restricted artery.

FIGS. 9–12 illustrate alternate embodiments of coil 124. As shown in FIG. 9, one embodiment of coil 124a is preferably formed of dual tubular members 132, 134 extending in essentially parallel relation and coupled at their distal ends to form a continuous essentially "U" shaped circuit. Coil 124 is preferably integrally formed as a unitary member. The tubular members 132 and 134 define an elongated conductive portion 136 and an inner conduit 138. Terminals of a frequency generator 126 are coupled to proximal ends of tubular members 132 and 134 to provide an RF signal through members 132 and 134. A distal end of the coil 124a includes shield 139. The distal end of the coil 124a is aligned relative to ring 120 of a vessel graft 86 and a vessel to be fused and RF generator 126 supplies current to coil 124a to induce a current in ring 120.

A coolant source 140 is coupled to conduit 138 to provide coolant fluid along the length of coil 124a. Coolant is pumped into and through continuous conduit 138 and discharged from conduit 138 at the proximal end of the coil 124a. In particular, coolant is pumped into conduit 138 formed by member 132 and discharged from conduit 138 formed by member 134. Coolant is inserted through members 132, 134 to remove heat generated at the coil/vessel interface to limit tissue temperature increase along coil 124 to maintain a healthy vessel. The coolant may be a saline or other suitable solution. Discharged coolant may be recycled to the coolant supply.

Figure 10:
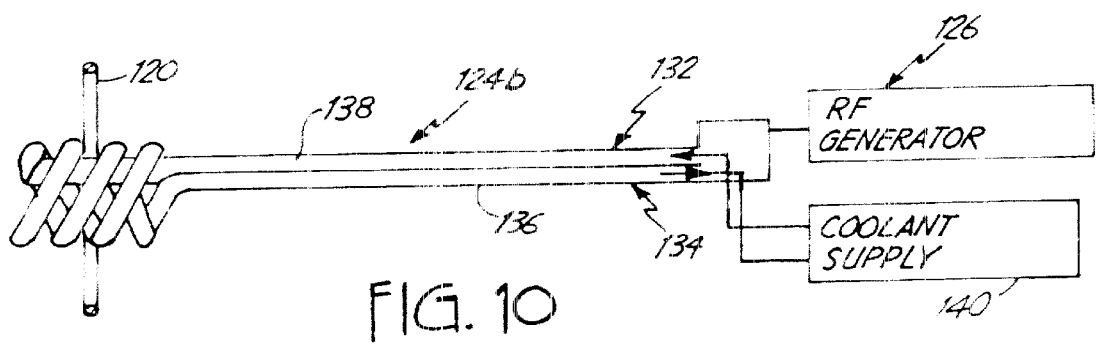

FIG. 10 illustrates another alternate embodiment of coil 124b similar to coil 124a of FIG. 9, where like numbers are used to identify like parts. The design of the distal end of the coil 124b differs from coil 124a and includes a spiral shaped extent at the distal end, which wraps around one of the elongated tubular members 132 to define a radiative end. The radiative end is positioned relative to ring 120 for inducing a current in ring 120 for fusing the vessel graft 86 to the restricted vessel 16.

Figure 11:
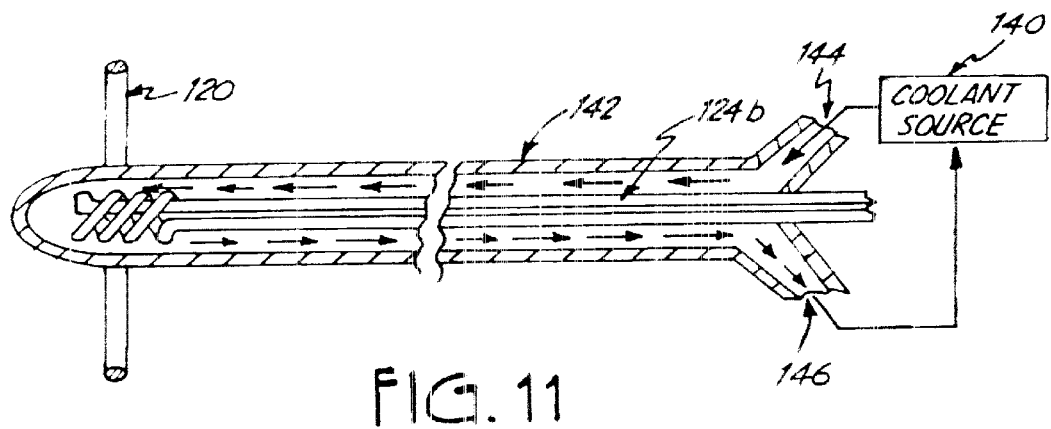
FIG. 11 illustrates an embodiment of an inductive coil for heating a ring for fusing a vessel graft to a restricted artery with a coolant delivery system shown in cross-section.

FIG. 11 illustrates an alternate embodiment of a coolant delivery system which is external to coil 124. Although, coil 124b is shown in FIG. 11, use of the external coolant delivery system is not limited to coil 124b. Thus, conduit 138 of coil 124b is not used for coolant delivery. The coolant delivery system is formed of a separate catheter 142 having a fluid inlet 144 and a fluid outlet 146. Coil 124 is housed in a lumen of catheter 142 and coolant is delivered from a coolant source 140 to fluid inlet 144 for cooling coil 124 in the lumen of the catheter 142. Coolant is cycled along the length of the catheter 142 and coil 124 and discharged from catheter 142 at outlet 146.

Figure 12:
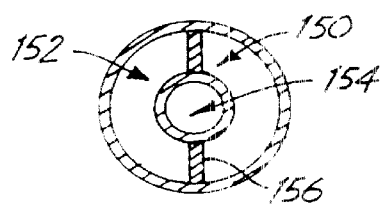
FIG. 12 is a cross sectional view of a coolant delivery system.

FIG. 12 is a cross-sectional view of an embodiment of a separate coolant delivery system which includes an elongated multilumen catheter. The multilumen catheter includes a delivery lumen .150, a discharge lumen 152 and a central lumen 154. Coil 124 is inserted and housed in the central lumen 154. Coolant is pumped into the delivery lumen 150.

Delivery lumen 150 and discharge lumen 152 are fluidly coupled at the distal end of the catheter so that fluid flowing through the delivery lumen 150 is discharged through the discharge lumen 152. In particular, delivery lumen 150 and discharge lumen 152 are formed via wall or section 156 which extends from the circular wall of the catheter along the length of the catheter to a distance spaced from the distal end of the catheter to provide flow space between the delivery lumen 150 and the discharge lumen 152 at the distal end of the catheter. Thus, as described, vessel graft 86 is fused to a restricted vessel.

Figure 13A:
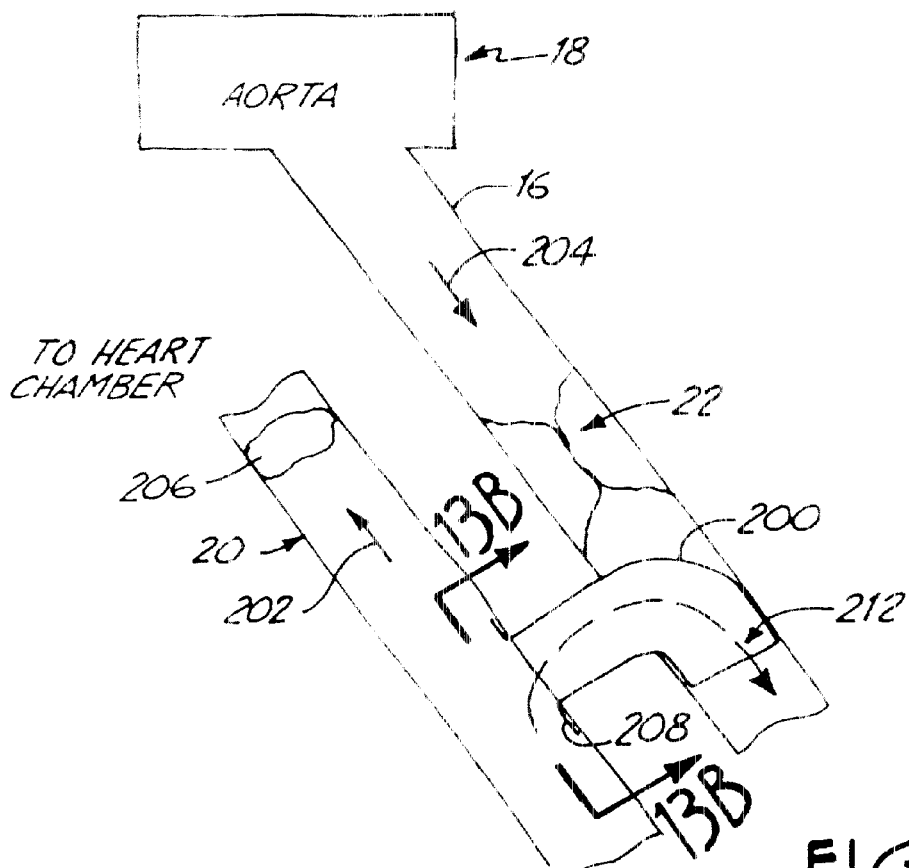
FIGS. 13A–13B illustrate an alternate embodiment of a bypass system according to the present invention.
Figure 13B:
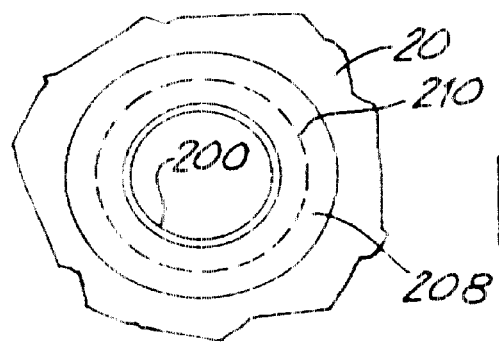

FIGS. 13A–13B illustrate an alternate embodiment of a bypass system of the present invention. As shown, the bypass system includes a conduit 200 which extends through apertures in the venous vessel 20 and arterial vessel 16 distal of the restriction 22. Thus, blood flow is provided in the restricted artery 16 distal of the restriction 22 via blood flow from the venous vessel 20.

In particular, blood flow in the venous vessel 20 flows to the heart as illustrated by arrow 202 and blood flow in artery 16 flows from the aorta 18 as illustrated by arrow 204. Venous vessel 20 includes a restriction 206 proximal of the restriction 22 in artery 16. Thus, blood flow through the venous vessel 20 to the heart 18 is occluded so that blood from the venous vessel 20 is directed from the venous vessel 20 through conduit 200 to the restricted artery distal 16 of the restriction 22. Thus, blood is supplied to the restricted artery 16 via the venous vessel 20.

Conduit 200 and restriction 206 are formed in a manner similar to that described for the embodiment illustrated in FIG. 2. The restriction 22 is located by inserting a guide device 40 into the artery 16. Thereafter a cutting device 56 is used to form apertures in the venous wall and artery wall distal of the restriction 22. The cutting device 56 may be inserted into the venous vessel 20 (and not the arterial vessel 16) since only one aperture is formed distal of the restriction.

Thereafter a graft 86 forming conduit 200 is inserted through the apertures via an introducer 88 inserted through venous vessel 20. A first end of the graft includes a stent and is secured to the arterial wall in a manner similar to that described for securing stent 94 in FIGS. 6C–6E. An annular ring 208 is formed by a second opposed end of the graft. The annular ring 208 is sutured such as by stitches 210 to the venous wall by a suturing process, previously described.

After the conduit 200 connects the venous vessel 20 to the arterial vessel 16, an occlusion forming device 50 is inserted into the venous vessel to form the proximal occlusion 206 for directing blood flow from venous vessel 20 through conduit 200 as illustrated by arrow 212. It should be understood that the procedure for performing the bypass of FIGS. 8A–8B is not limited to that described and that the cutting device may form apertures as well as provide a device for positioning the graft to form conduit 200 as described.

Figure 14A:
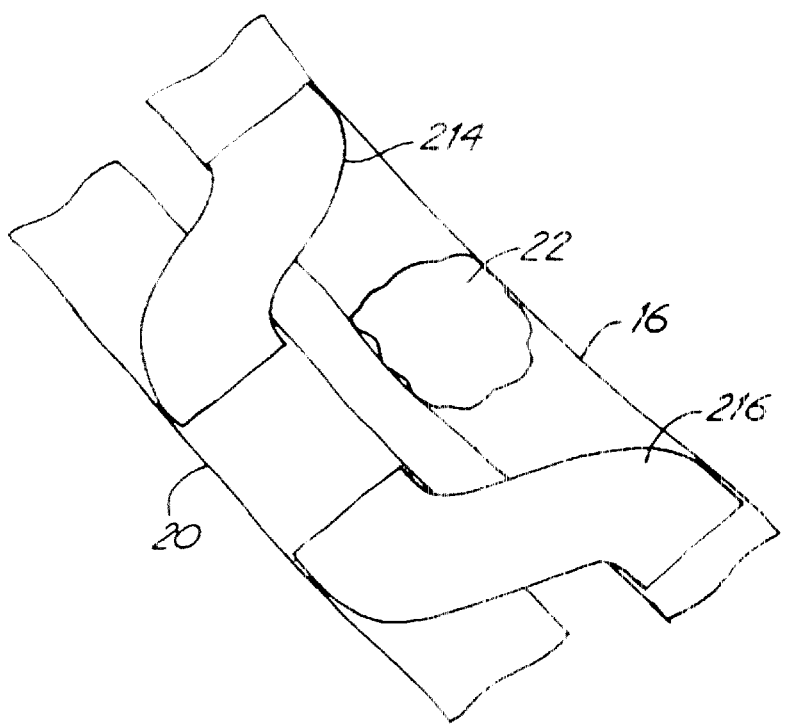
FIGS. 14A and 14B illustrate other alternate embodiments of a bypass system according to the present invention.

FIG. 14A illustrates yet another embodiment in accordance with the present invention. In FIG. 14A, rather than using one stent graft to bypass restriction 22 in artery 16, a pair of separate grafts are used. FIG. 14A illustrates deployment of a proximal graft 214 which fluidly couples the interior or a proximal portion of artery 16 with the interior of vein 20. FIG. 14A also shows a distal graft 216 which couples the interior portion of vein 20, distal of graft 214, with a portion of artery 16 distal of restriction 22. The apertures formed in the walls of vessels 16 and 20, and the deployment of grafts 214 and 216 is similar to that shown with respect to FIGS. 4A–6E.

Figure 14B:
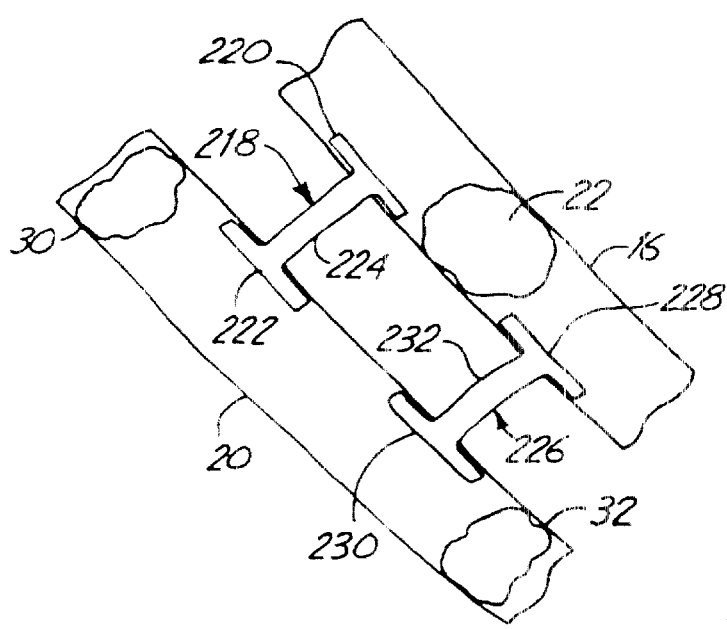

FIG. 14B shows yet another embodiment according to the present invention. FIG. 14B illustrates a pair of grafts or conduits which are used to bypass restriction 22 in artery 16. A proximal conduit 218 is provided which has a pair of annular rims 220 and 222. The annular rims are attached to a graft material 224 which extends therebetween. Annular rims 220 and 222 are secured to the lumen walls of vessel 16 and 20, respectively, in a fashion similar to that shown in FIG. 8B.

Distal conduit 226 is also illustrated in FIG. 14B. Distal conduit 226 is similar to proximal conduit 218, and includes two annular rims 228 and 230 which are connected to a graft material 232. Also, in the embodiment shown in FIG. 14B, the vessel 20, itself, and without any graft running therethrough, forms the bypass around restriction 22. Therefore, FIG. 14D illustrates occlusions 30 and 32 to preclude drainage flow through vein 20.

Thus, the present invention involves a system by which coronary artery bypass procedures can be executed substantially percutaneously and transluminally. This serves to significantly reduce the disadvantages associated with prior treatment techniques. In the embodiment in which a venous vessel is used to form the conduit providing blood flow, the present invention eliminates half of the intraluminal connections required in a typical graft procedure. Further, since the present invention utilizes a venous vessel, it is relatively easy to occlude blood flow in the relevant vasculature (i.e., in the venous vasculature and the occluded vasculature). This occlusion is relatively easy as opposed to the necessity of occluding blood flow throughout the entire aorta in systems which provide a graft directly from the aorta.

Also, while the present invention has been described with respect to coronary arteries and associated veins, it can be employed in any suitable artery and vein.

Although the present invention has been described with reference to preferred embodiments, workers skilled in the art will recognize that changes may be made in form and detail without departing from the spirit and scope of the invention.

What is claimed is:

1. A method of bypassing a restriction in a mammal via a vessel graft comprising:

positioning a conductive ring about an attachment portion of the vessel graft prior to intraluminally inserting the graft;

forming apertures through a venous vessel and a restricted artery at a desired location;

intraluminally inserting the vessel graft to align the attachment portion relative to the aperture of the restricted artery; and inductively heating the conductive ring to fuse attachment of the vessel graft to the restricted artery.

2. The method of claim 1 wherein the method for inductively heating the conductive rings comprises:

providing an inductive coil;

intraluminally inserting the inductive coil and advancing the inductive coil for alignment with the conductive ring at the attachment portion of the vessel graft; and supplying a signal to the coil for inducing a current in the conductive ring.

3. The method of claim 2 wherein a radio frequency generator is coupled to the inductive coil for providing a signal.

4. The method of claim 2 and further comprising:

supplying a coolant solution to the inductive coil while supplying the signal.

5. The method of claim 4 wherein the method for supplying the coolant solution comprises:
 providing a coolant delivery system including a delivery conduit coupled with the coil;
 supplying coolant through the delivery conduit to cool the coil; and
 providing a discharge conduit for discharging fluid from the delivery conduit.

6. The method of claim 5 wherein the inductive coil is formed of a hollow tubular member, the tubular member of the inductive coil defining the delivery conduit and discharge conduit of the coolant delivery system.

7. The method of claim 5 wherein the coolant delivery system and inductive coil are separately formed.

8. A method for attaching a graft to a vessel in a mammal comprising steps of:
 positioning the graft relative to a vessel portion and a conductive ring between the graft and the vessel portion; and
 inductively heating the conductive ring to fuse the graft to the vessel portion.

9. The method of claim 8 wherein the vessel portion includes an opened flap formed by a cut portion of the vessel wall.

10. The method of claim 8 wherein the step of inductively heating the conductive ring includes:
 inserting an inductive heating coil and aligning the inductive heating coil relative to the conductive ring; and
 energizing the inductive heating coil to inductively heat the conductive ring.

11. The method of claim 10 wherein the inductive heating coil is energized by a radio frequency generator.

12. The method of claim 8 and further comprising:
 supplying a coolant while inductively heating the conductive ring.

* * * * *